United States Patent [19]

Besecke et al.

[11] Patent Number: 4,652,656
[45] Date of Patent: Mar. 24, 1987

[54] UV-ABSORBING MONOMER AND POLYMERS THEREOF

[75] Inventors: Siegmund Besecke, Seeheim-Jugenheim; Ralf Liebler, Darmstadt; Heinz-Juergen Hohage, Muehltal; Guenter Schroeder, Ober-Ramstadt, all of Fed. Rep. of Germany

[73] Assignee: Röhm GmbH, Darmstadt, Fed. Rep. of Germany

[21] Appl. No.: 851,254

[22] Filed: Apr. 14, 1986

Related U.S. Application Data

[62] Division of Ser. No. 787,660, Oct. 16, 1985, Pat. No. 4,612,358.

[30] Foreign Application Priority Data

Oct. 27, 1984 [DE] Fed. Rep. of Germany ....... 3439483

[51] Int. Cl.⁴ ............................................ C07D 249/16
[52] U.S. Cl. .................................... 548/261; 526/259
[58] Field of Search ......................... 548/261; 526/259

[56] References Cited

U.S. PATENT DOCUMENTS 3,399,173  8/1968  Heller et al. ...................... 526/259

Primary Examiner—Paul R. Michl
Assistant Examiner—Alex H. Walker
Attorney, Agent, or Firm—Curtis, Morris & Safford

[57] ABSTRACT

UV absorbing compounds, susceptible to free-radical polymerization, of the formula

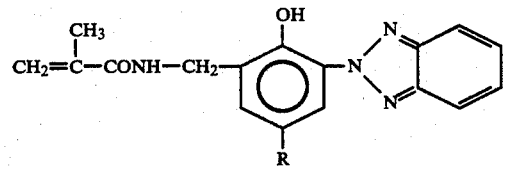

wherein R is alkyl having from 4 to 12 carbon atoms of which not more than 6 are present in a linear chain, and in particular
2-(2'-hydroxy-3'-methacrylamidomethyl-5'-tert-octylphenyl)benzotriazole, and polymers thereof.

2 Claims, No Drawings

UV-ABSORBING MONOMER AND POLYMERS THEREOF

This application is a division of application Ser. No. 787,660, filed Oct. 16, 1985, now U.S. Pat. No. 4,612,358.

The present invention relates to certain polymerizable ultraviolet absorbing compounds of the formula

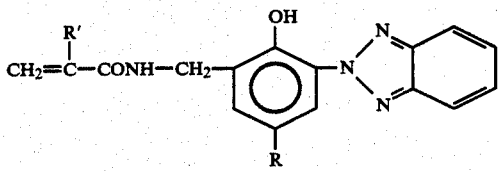

and to ultraviolet absorbing polymers prepared therefrom. More in particular, the invention relates to those compounds wherein $R^1$ is methyl and R is $(C_4-C_{12})$-alkyl having no more than six carbon atoms in a linear (unbranched) chain.

The monomeric compounds of the invention and their polymers have a strongly absorbing effect for ultraviolet radiation of wavelengths up to about 400 nm. Such radiation has a damaging effect on many important engineering plastics. To protect plastics sensitive to ultraviolet radiation, polymerizable UV absorbers are incorporated in them or are applied, in the form of their polymers, as a protective layer to the surface of these plastics.

Many compounds of the above formula where R' is a hydrogen atom are known from U.S. Pat. No. 3,399,173. These compounds are derivatives of acrylamide. Polymers of these compounds are relatively soft and their Vicat softening point is so low that they are usually not suitable for use as engineering plastics. Their copolymers with methacrylic monomers are considerably softer or have a lower Vicat softening point than do the homopolymers of the methacrylic monomers or of styrene.

From the same patent, other derivatives of the aforementioned methacrylamides are also known wherein R' is methyl and R is either methyl or long chain alkyl, for example, n-octyl or n-dodecyl. These polymerizable UV absorbers are also unsuitable for the production of ultraviolet absorbing plastics comprising copolymers of methacrylic monomers or of styrene since the compound where R is methyl does not sufficiently dissolve in methacrylic monomers and in styrene and the compounds with long chain groups R have the same softening effect as the acrylamide derivatives mentioned earlier, where R' is hydrogen.

Surprisingly, it has now been found that compounds of the aforementioned formula wherein R' is methyl and R is alkyl having from 4 to 12 carbon atoms of which not more than 6 are arranged in a continuous unbranched (linear) chain are readily soluble in most unsaturated vinyl or vinylidene monomers, and particularly in methacrylic monomers and in styrene, and, moreover, do not have a pronounced softening effect on copolymers with these monomers. Even with relatively high contents of units derived from the UV absorbers of the invention, these copolymers possess valuable synthetic resin properties.

The undesirable softening effect of the prior art UV absorbers seems to occur whenever, in the compounds of the formula, R' is methyl, R is alkyl having more than 5 unbranched carbon atoms, for example a n-octyl or n-dodecyl group, or R contains such a group.

The preferred compounds of the invention are those which have from 6 to 12, and more particularly from 8 to 10 carbon atoms in the group R. The tert.-octyl derivative having a group R of the structure

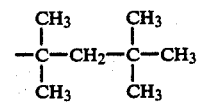

has proved particularly advantageous. Further examples of the new UV absorbers are compounds wherein R is tert.-butyl, tert.-amyl, n-hexyl, cyclohexyl, or tri-isobutyl. The advantage offered by the new UV absorbers is apparent from a comparison of the Vicat softening points (VSP) of various copolymers (with molecular weights ranging from 100 to 100,000, as determined by gel permeation chromatography) of 80 weight percent methyl methacrylate and 20 weight percent of a compound of the aforementioned formula:

|  | Compound of formula (I) | | VSP (DIN 53460) |
| --- | --- | --- | --- |
|  | (R) | (R') | (°C.) |
| In accordance with the invention | tert.-Octyl | Methyl | 108 |
| For comparison: | Polymethyl methacrylate |  | 108–109 |
|  | n-Octyl | Methyl | 102 |
|  | tert.-Octyl | Hydrogen | 80 |
|  | n-Octyl | Hydrogen | 73 |

The new UV absorbers can be prepared by processes analogous to those of the prior art compounds. The reaction of N-methylolacrylamide or its alkyl esters with 2-(2'-hydroxy-5'-alkylphenyl)benzotriazoles of the formula

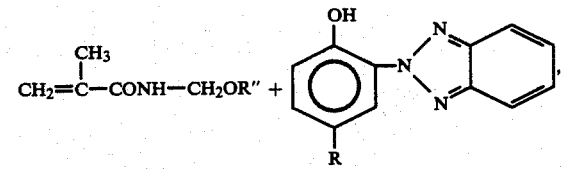

wherein R has the meaning given earlier and R" is hydrogen or alkyl preferably containing from 1 to 4 carbon atoms, is preferred. When acid catalyzed with concentrated sulfuric acid as the reaction medium, the reaction proceeds in the temperature range from 0° C. to 50° C. with good yields.

The new UV absorbers lend themselves to the production of UV absorbing copolymers. To this end, they are conventionally exposed, when in admixture with other vinyl or vinylidene monomers, to the action of an initiator which generates free radicals. Preferred vinyl or vinylidene monomers are styrene and methacrylic monomers. The latter include methacrylonitrile and monomers with the group $CH_2=C(CH_3)-CO-$, and particularly alkyl esters of methacrylic acid which preferably contain from 1 to 4 carbon atoms in the alkyl group. Copolymers with hydroxyalkyl methacrylates also possess interesting technical properties. Methyl methacrylate is particularly preferred. These preferred monomers usually represent 50 weight percent or more of the copolymer. Suitable further comonomers are acrylonitrile, esters of acrylic acid, vinyl esters, vinyl halides and, in minor amounts, special monomers having particular functional groups.

The but slightly softening effect of the new UV absorbers is manifest especially in copolymers which have a Vicat softening point of over 100° C. and which include more than 3 weight percent of the new UV absorbers.

The amount of these UV absorbers incorporated in the copolymers will depend on the intended effect. When the copolymer serves as a UV-protective layer for a plastic that is sensitive to ultraviolet radiation, then polymers containing more than 10 weight percent, and in particular from 20 to 60 weight percent, of the UV absorbing monomer will be suitable. If, however, the plastic itself is to be protected, then the proportion of the UV absorber will generally be less than 10 weight percent, and usually less than 1 percent. As a rule, a proportion of UV absorber of less than 0.05 weight percent will not provide adequate protection.

A better understanding of the invention and its many advantages will be had by referring to the following specific examples, given by way of illustration.

EXAMPLES (A) Preparation of a polymerizable UV absorber 900 ml of 96–98 percent sulfuric acid are introduced into a 2-liter multinecked flask equipped with stirrer and internal thermometer and 322.1 g (1 mole) of 2-(2-hydroxy-5-tert-octylphenyl)benzotriazole ("Cyasorb UV 5411", a product of American Cyanamid Co.) is dissolved therein. A yellow solution forms. The latter is held at 15° C. to 20° C. and mixed in portions with 120.4 g (1.05 moles) of 98 percent hydroxymethylmethacrylamide. On completion of this addition, the reaction mixture is allowed to react further for 2.5 hr. at room temperature. The mixture is then dripped with vigorous stirring into about 3 liters of ice water. The pale yellow reaction product precipitates. The precipitate is filtered off by suction and washed neutral with a saturated aqueous sodium bicarbonate solution. The substance is then washed with distilled water, vigorously filtered off by suction, and dissolved in about 2 liters of methylene chloride. The organic phase is successively extracted from 2 to 3 times with distilled water, dried with Na$_2$SO$_4$, filtered, mixed with 0.015 g of 2,2,6,6-tetramethylpiperidine N-oxide radical (a polymerization inhibitor) and concentrated so far as possible in a rotary evaporator under a water jet vacuum at not more than 50° C. The remaining substance is suspended in hexane and filtered off by suction. To remove the slight yellow coloration of the crystals, the product is mixed with a little methanol and then filtered off by suction. The crystals are rewashed with hexane and the product is then dried to constant weight at room temperature. Yield: 355 g (81.1% of theory) of 2-(2'-hydroxy-3'-methacrylamidomethyl-5'-tert-octylphenyl)benzotriazole.

| Analysis of reaction product: | | | |
|---|---|---|---|
| | % C | % H | % N |
| Calculated | 71.4 | 7.6 | 13.3 |
| Found | 71.2 | 7.6 | 13.3 |

(B) Preparation of bulk polymers 20 parts of the compound prepared as described under (A) are dissolved in 80 parts of weight of methyl methacrylate (MMA) with stirring and heating to 50° C. 0.1 part of dilauroyl peroxide and 0.4 part of dodecyl mercaptan are added. The mixture is filtered and, after degasifying in a vacuum, is filled into a foil bag which is closed with the exclusion of air. For polymerization of the mixture, the foil bag is placed for 20 hours in a water bath at 50° C. and for 8 hours in a heating cabinet at 100° C. In the Table which follows, the polymer so obtained is designated as "I".

A mixture of 99.5 parts by weight of methyl methacrylate and 0.5 part of the UV absorber prepared as described under (A) is prepared in the same manner. The resulting polymer is designated "II".

For comparison, two further bulk polymers "III" and "IV" are produed in the same manner, except that in place of the compound prepared as described under (A), wherein R represents tert-octyl, the known analogous compound with R being n-octyl is used. As may be seen from the following Table, the polymers so produced have a significantly lower Vicat softening point (VSP).

TABLE

| No. | Proportion MMA, (%) | Proportion (%) | UV absorber (R) | Reduced viscosity (ml/g) | VSP (°C.) |
|---|---|---|---|---|---|
| I | 80 | 20 | tert-Octyl | 45 | 108 |
| II | 99.5 | 0.5 | tert-Octyl | 50 | 109 |
| III | 80 | 20 | n-Octyl | 40 | 102 |
| IV | 99.5 | 0.5 | n-Octyl | 50 | 106 |

(C) Preparation of a bead polymer

A mixture of 250 parts by weight of the polymerizable UV absorber prepared as described under (A) and 250 parts of methyl methacrylate, 2.5 parts of dilauroyl peroxide, and 1.5 parts of n-dodecyl mercaptan are added at 75° C. with stirring to 1000 parts by weight of water phase containing 0.2 percent (based on the water phase) of aluminum hydroxide as dispersant and, for improvement of the dispersant action, 5 percent (based on the aluminum hydroxide) of a sodium ($C_{14}$–$C_{16}$)alkyl sulfonate, present in a 2-liter round-neck flask equipped with reflux condenser, thermometer, and stirrer, and suspended to form droplets. After a polymerization time of 60 minutes at 78°–80° C. and 60 minutes at 84°–86° C., the bead polymer is washed with water on a nutsch filter and dried for about 20 hours at 50° C.

The copolymer is obtained in a yield of 99 percent. The average particle size is 100 microns. The reduced viscosity of the polymer is 44 ml/g and its Vicat softening point is 100° C.

For comparison, a bead polymer is prepared under the same conditions using a corresponding amount of 2-(2'-hydroxy-3'-methacrylamidomethyl-5'-n-octylphenyl)-benzotriazole in place of the tert-octylphenyl derivative of the invention. The reduced viscosity of the bead polymer is 60 ml/g and its Vicat softening point is 82° C.

We claim:

1. A compound of the formula

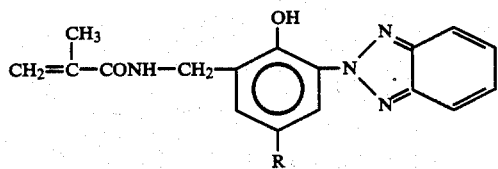
wherein R is alkyl having from 4 to 12 carbon atoms not more than 6 of which are present in an unbranched chain.
2. A compound as in claim 1 which is 2-(2'-Hydroxy-3'-methacrylamidomethyl-5'-tert-octylphenyl)benzotriazole.
* * * * *